US010317383B2

(12) United States Patent
Schreiber et al.

(10) Patent No.: US 10,317,383 B2
(45) Date of Patent: Jun. 11, 2019

(54) MOBILE BASED COLLECTION OF WATER QUALITY MEASUREMENT DATA

(71) Applicant: Hach Lange GmbH, Berlin (DE)

(72) Inventors: Max Schreiber, Berlin (DE); Johannes Berssen, Panketal (DE); Sylvia Haustein, Berlin (DE); Jan Bob, Krefeld (DE)

(73) Assignee: HACH LANGE GMBH, Berlin (DE)

( * ) Notice: Subject to any disclaimer, the term of this patent is extended or adjusted under 35 U.S.C. 154(b) by 328 days.

(21) Appl. No.: 14/811,646

(22) Filed: Jul. 28, 2015

(65) Prior Publication Data

US 2016/0033465 A1 Feb. 4, 2016

Related U.S. Application Data

(60) Provisional application No. 62/030,441, filed on Jul. 29, 2014.

(51) Int. Cl.
*G01F 17/00* (2006.01)
*G01N 33/18* (2006.01)
(Continued)

(52) U.S. Cl.
CPC ....... *G01N 33/18* (2013.01); *G01N 35/00623* (2013.01); *G01N 35/00732* (2013.01);
(Continued)

(58) Field of Classification Search
CPC ..... G01N 35/000623; G01N 35/00742; G01N 2035/00752
See application file for complete search history.

(56) References Cited

U.S. PATENT DOCUMENTS 4,811,249 A * 3/1989 Marsh .................... G01D 9/005
341/50
2010/0083730 A1* 4/2010 Le ........................ G01K 3/005
73/1.02
(Continued)

FOREIGN PATENT DOCUMENTS

CN 201729262 2/2011
CN 102324055 1/2012
(Continued)

OTHER PUBLICATIONS

CN Office Action, dated Jun. 15, 2018. pages 6 <untranslated>.
(Continued)

*Primary Examiner* — Matthew G Marini
(74) *Attorney, Agent, or Firm* — Ference & Associates LLC

(57) ABSTRACT

Methods and arrangements for collecting data related to a water quality sample location. Identifying information of a water quality sample container is electronically obtained, and identifying information of a water quality sample location is electronically obtained. There is placed, in the container, a water sample from the water quality sample location. There is stored the identifying information of the water quality sample container and the identifying information of the water quality sample location; such storing includes associating the identifying information of the water quality sample container and the identifying information of the water quality sample location. Other variants and embodiments are broadly contemplated herein, including methods and arrangements for validating water quality sample data.

19 Claims, 9 Drawing Sheets

(51) Int. Cl.
G06F 16/22 (2019.01)
G06F 16/955 (2019.01)
G01N 35/00 (2006.01)
G01N 1/10 (2006.01)
G01N 1/02 (2006.01)

(52) U.S. Cl.
CPC .......... *G06F 16/22* (2019.01); *G06F 16/9554* (2019.01); *G01N 1/10* (2013.01); *G01N 2001/021* (2013.01)

(56) References Cited

U.S. PATENT DOCUMENTS

2012/0091008 A1* 4/2012 Muir .................... G01N 27/333 205/316
2013/0104633 A1* 5/2013 Zangenberg ............. G01N 1/10 73/61.59
2013/0316461 A1* 11/2013 Fujita ................. G01N 33/5005 436/63
2014/0172349 A1* 6/2014 Harle .................. G01K 15/005 702/130

FOREIGN PATENT DOCUMENTS

WO WO01/94937 12/2001
WO WO2012/069688 5/2012

OTHER PUBLICATIONS

CN Office Action, dated Jun. 15, 2018. pages 8 <translated>.
European Patent Office, Communications pursuant to Article 94(3) EPC, dated May 3, 2018, pages 7.
International Search Report, dated Feb. 5, 2016, pages 3.
International Searching Authority, Written Opinion of the International Searching Authorirty, dated Feb. 2, 2016, pages 6.

* cited by examiner

MOBILE BASED COLLECTION OF WATER QUALITY MEASUREMENT DATA

CLAIM FOR PRIORITY

This application claims the benefit of U.S. Provisional Patent Application Ser. No. 62/030,441, filed on Jul. 29, 2014, entitled "MOBILE-BASED COLLECTION OF WATER QUALITY MEASUREMENT DATA", which is incorporated by reference in its entirety herein.

BACKGROUND

Accurate analysis of fluids is important to many industries. By way of example, in the provision and propagation of drinking water, it is considered important to obtain accurate measurements of different parameters such as alkalinity and/or turbidity, as sensed or sampled at different locations. Some such locations can involve different points along a natural watercourse that feeds into a water supply, while other such locations can involve different points in the (post-treatment and filtration) propagation network of the water supply itself. Alkalinity is a required reporting parameter for many regulatory agencies such as the Environmental Protection Agency (EPA) and the Food and Drug Administration (FDA); the EPA has listed pH as a secondary drinking water regulation. Turbidity is a measure of the cloudiness or haziness of a fluid (e.g., that may be contributed to be individual particles) and thus is considered to provide a reliable measurement of water quality. Turbidity is measured in nephelometric turbidity units (NTUs), and different regulatory standards may apply for quantitative measures of NTUs at different points of a water supply network (which, again, could include one or more watercourses that feed into a water supply, or different points in a propagation network, alike).

To measure one or more parameters related to water quality at different points of a water supply network, sensors may be placed to obtain direct measurements. Thus, for instance, Secchi disks or turbidity tubes may be used to measure turbidity in watercourses or reservoirs, or even in points of a water propagation network. Measurements from these can be electronically transmitted to a data logger (which, for instance, can accept data from five to ten sensors), via a wired or wireless connection. However, reliability of the sensors may need to be ensured via an additional check of water samples at another measuring device. Such a measuring device may be disposed in a fixed or mobile laboratory, or can be portable to take measurements at or near the location of a sensor. When conducting such an additional check, a comparison can be made with one or more measurements from a sensor (e.g., itself taken at the same time that a water sample is collected for the additional check) and, if necessary, the sensor can be recalibrated based on the comparison.

Typically, a significant number of sensors at different points of a water supply network may need to be regularly checked and, if necessary, recalibrated. To accomplish this, it is typically the case that numerous water samples are collected in containers at the locations of such sensors, preferably at times coincident with one or more measurements being triggered and taken by a sensor. The containers are typically labeled by hand or via pre-printing, showing a visual/verbal indication of identifying information such as the location from which the sample is taken. However, there is typically nothing else to ensure that the sample in a container is clearly associated with a particular sensor and/or location. Simple human error may thus result in incorrect associations being made (between containers and sensors/locations), with the consequence of incorrect or misleading data (e.g., obtained at a laboratory) for sensor recalibration.

BRIEF SUMMARY

In summary, an embodiment provides an apparatus comprising: one or more processors; a program storage device tangibly embodying a program of instructions that when executed by the one or more processors enables the apparatus to: receive information related to the identification of a water quality sample container; receive information related to the identification of a predetermined water quality sample location; store the information related to the identification of the water quality sample container and the information related to the identification of the predetermined water quality sample location.

Additionally, an embodiment provides an apparatus comprising: one or more processors; a program storage device tangibly embodying a program of instructions that when executed by the one or more processors enables the apparatus to: receive information related to water quality contained with a water quality sample container; receive information related to identification of a predetermined water quality sample location; receive information related to water quality of a sample obtained from the predetermined water quality sample location; compare the information related to water quality contained with a water quality sample container and the information related to water quality of a sample obtained from the predetermined water quality sample location; and provide an indication of a result of the comparison.

Further, an embodiment provides a method comprising: electronically obtaining identifying information of a water quality sample container; electronically obtaining identifying information of a water quality sample location; placing, in the container, a water sample from the water quality sample location; and storing the identifying information of the water quality sample container and the identifying information of the water quality sample location; the storing comprising associating the identifying information of the water quality sample container and the identifying information of the water quality sample location.

Moreover, an embodiment provides a method comprising: receiving measurement data obtained by a water quality sensor; obtaining identifying information for a container which contains a water sample from a location measured by the water quality sensor; validating the water quality sensor via: matching the measurement data obtained by the water quality sensor with the identifying information for the container; testing the water sample from the container, and thereby obtaining additional measurement data; and comparing the measurement data obtained by the water quality sensor with the additional measurement data from the testing.

Yet further, an embodiment provides a program storage device storing program code executable by one or more processors, the program code comprising: program code configured to electronically obtain identifying information of a water quality sample container; program code configured to electronically obtain identifying information of a water quality sample location at which a water sample is placed in the container; and program code configured to store the identifying information of the water quality sample container and the identifying information of the water quality sample location, via associating the identifying information of the water quality sample container and the identifying information of the water quality sample location.

Yet additionally, an embodiment provides a program storage device storing program code executable by one or more processors, the program code comprising: program code configured to receive measurement data obtained by a water quality sensor; program code configured to obtain identifying information for a container which contains a water sample from a location measured by the water quality sensor; program code configured to validate the water quality sensor via: matching the measurement data obtained by the water quality sensor with the identifying information for the container; testing the water sample from the container, and thereby obtaining additional measurement data; and comparing the measurement data obtained by the water quality sensor with the additional measurement data from the testing.

Still further, an embodiment provides a kit comprising: a container for obtaining a water sample from a location measured by a water quality sensor, the container comprising electronically readable identifying information; and an apparatus which: receives measurement data from the water quality sensor and identifying information for the container; matches the measurement data from the water quality sensor with the identifying information for the container; obtains additional measurement data from testing of the water sample from the container; and validates the water quality sensor via comparing the measurement data from the water quality sensor with the additional measurement data.

Still additionally, an embodiment provides an apparatus comprising: a water quality sample container; a electronic storage medium physically associated with the water quality sample container; and an identifier which provides electronically readable identifying information of the water quality sample container; the electronic storage medium being configured to store information related to a water quality sample from a predetermined location.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Figure 1:
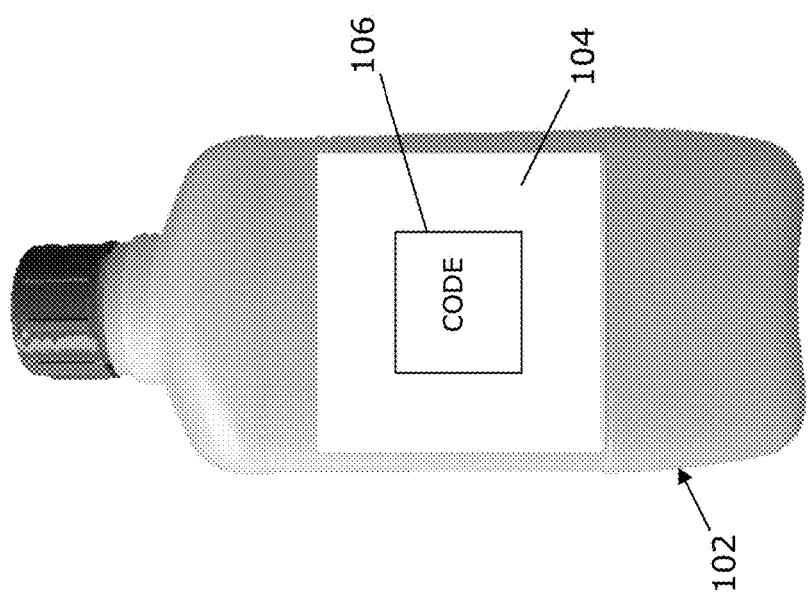
FIG. 1 provides an elevational view of a sample container.
Figure 6:
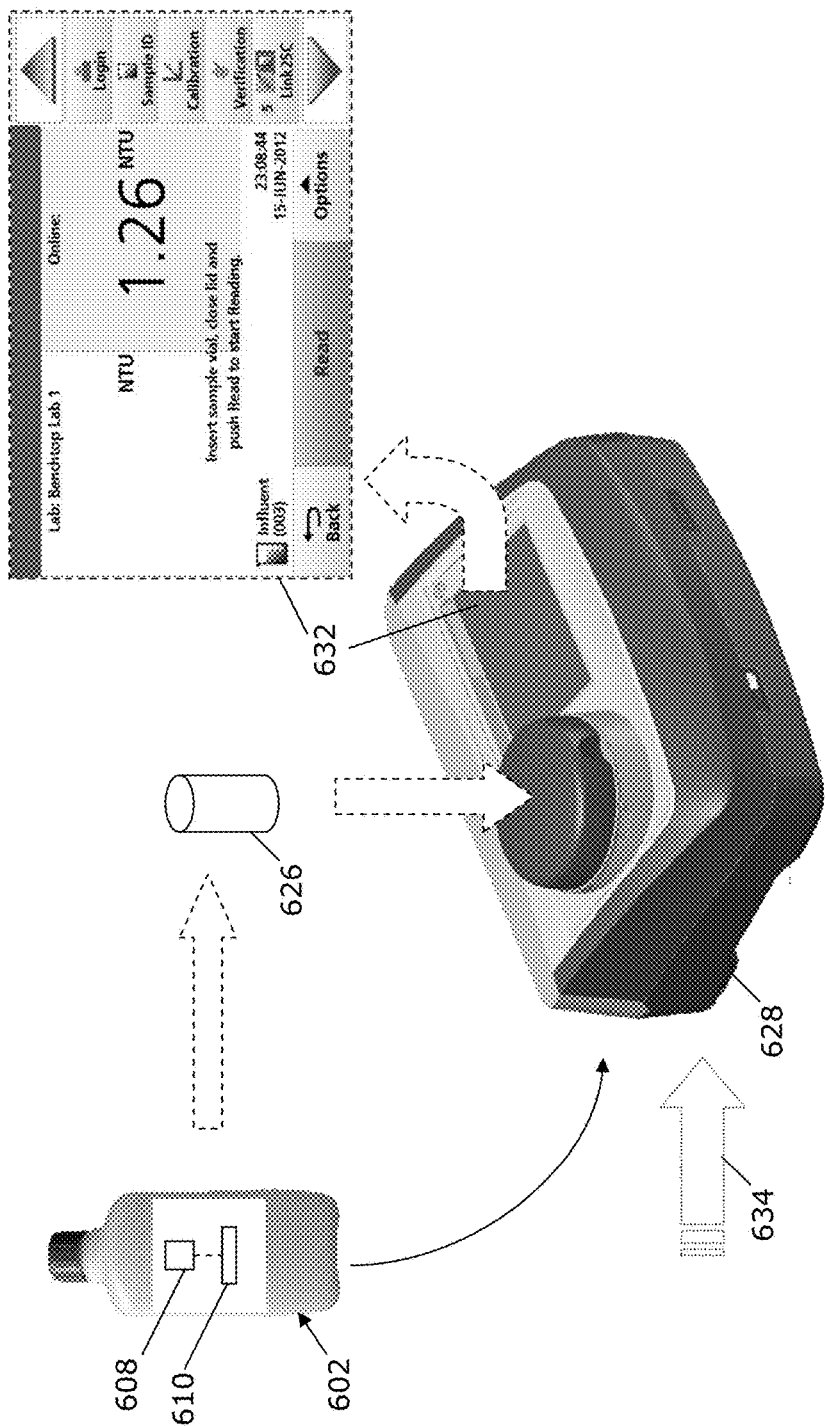
FIG. 6 schematically illustrates a working example of a variant embodiment of validating water quality sample data.
Figure 7:
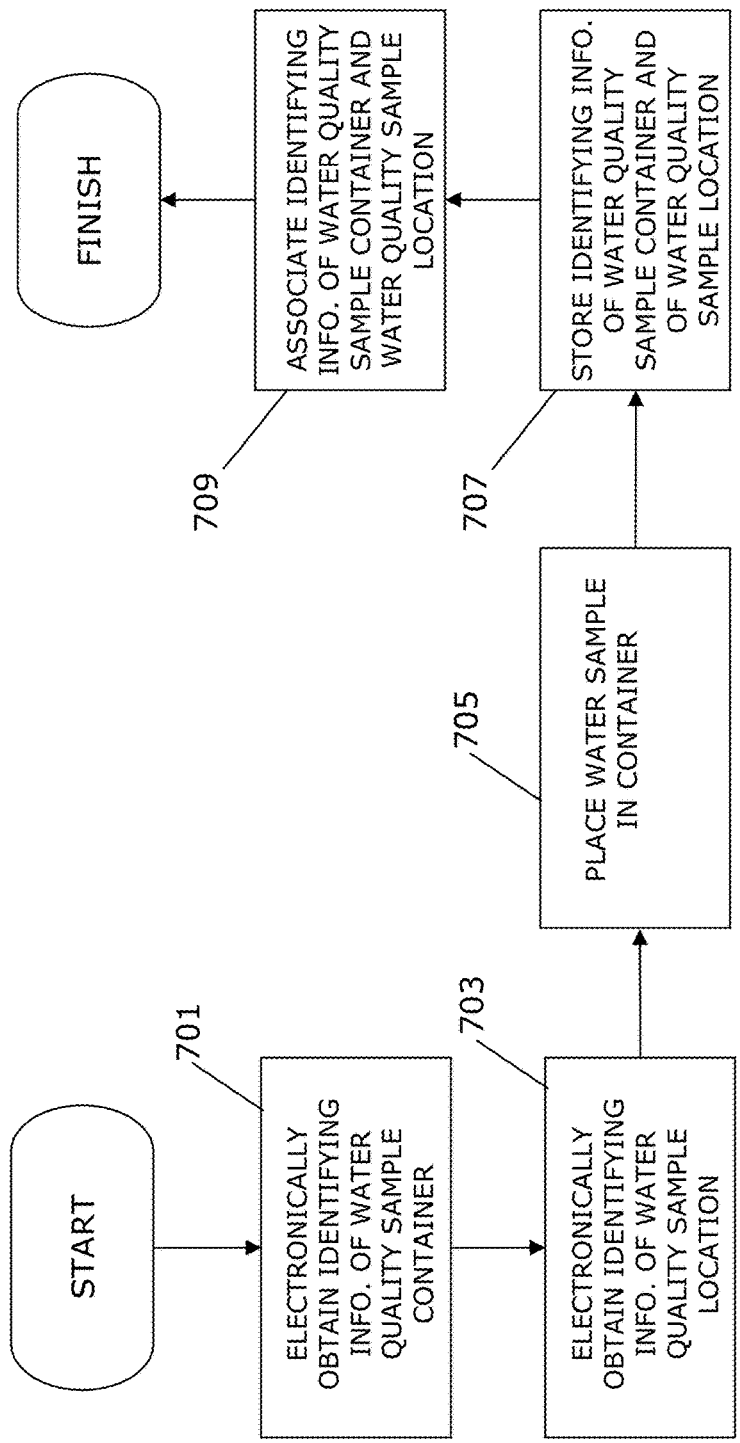
FIG. 7 sets forth a process more generally for collecting data related to a water quality sample location.
Figure 8:
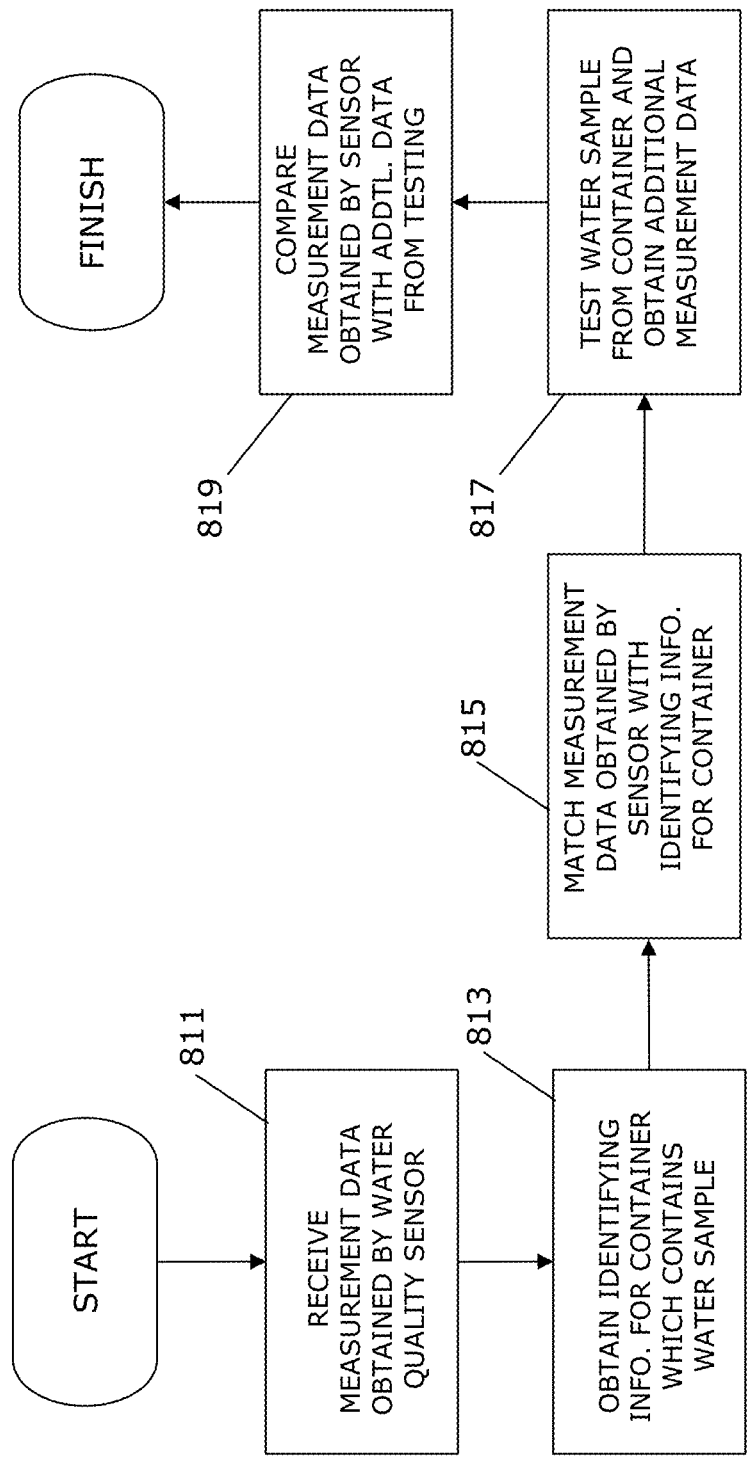
FIG. 8 sets forth a process more generally for validating water quality sample data.

To facilitate easier reference, in advancing from FIG. 1 to and through FIG. 8, a reference numeral is advanced by a multiple of 100 in indicating a substantially similar or analogous component or element with respect to at least one component or element found in at least one earlier figure among FIGS. 1-8.

FIG. 1 provides an elevational view of a sample container 102, in accordance with at least one embodiment of the invention. In a manner to be understood and appreciated more fully below, container 102 is used for containing a water sample from a location measured by a water quality sensor. For purposes of identifying the container 102, a label 104 includes an electronically readable code 106, such as a two-dimensional code (e.g., a QR [Quick Response] code). This is provided merely by way of illustrative and non-restrictive example; generally, optical (or optically readable) information on the label 104 can be read and translated into electronic information. Such optical information can be in the form of a QR code or other type of bar code.

Figure 2:
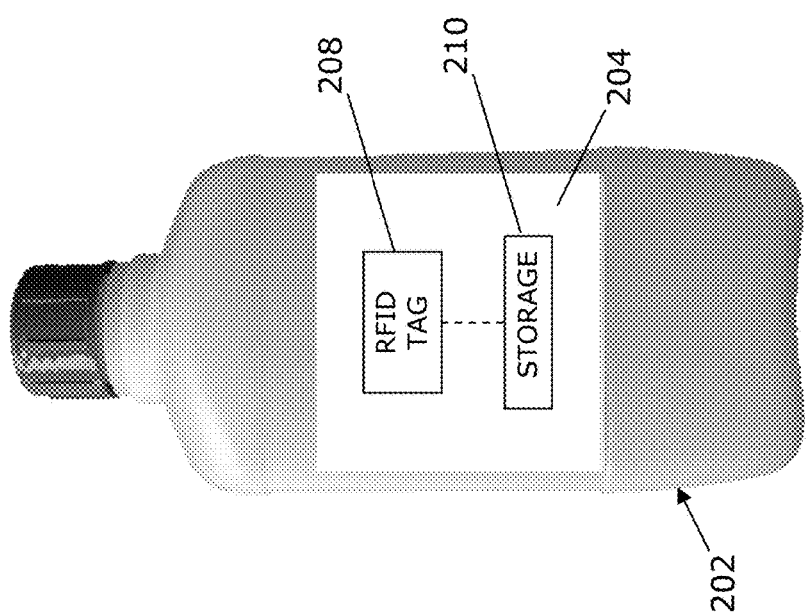
FIG. 2 provides an elevational view of a variant embodiment of a sample container.

FIG. 2 provides an elevational view of a variant embodiment of a sample container 202, in accordance with at least one embodiment of the invention. Here, for purposes of identifying the container 202, a label 204 includes an electronically readable RFID (radio frequency identification) tag 208. As will be further appreciated herebelow, tag 208 may include an associated storage capability (210), for the purpose of storing small amounts of data that can be portable with container 202. One non-restrictive example of a tag with such capabilities is a tag (e.g., unpowered chip) with NFC (near field communication) capabilities.

Figure 3:
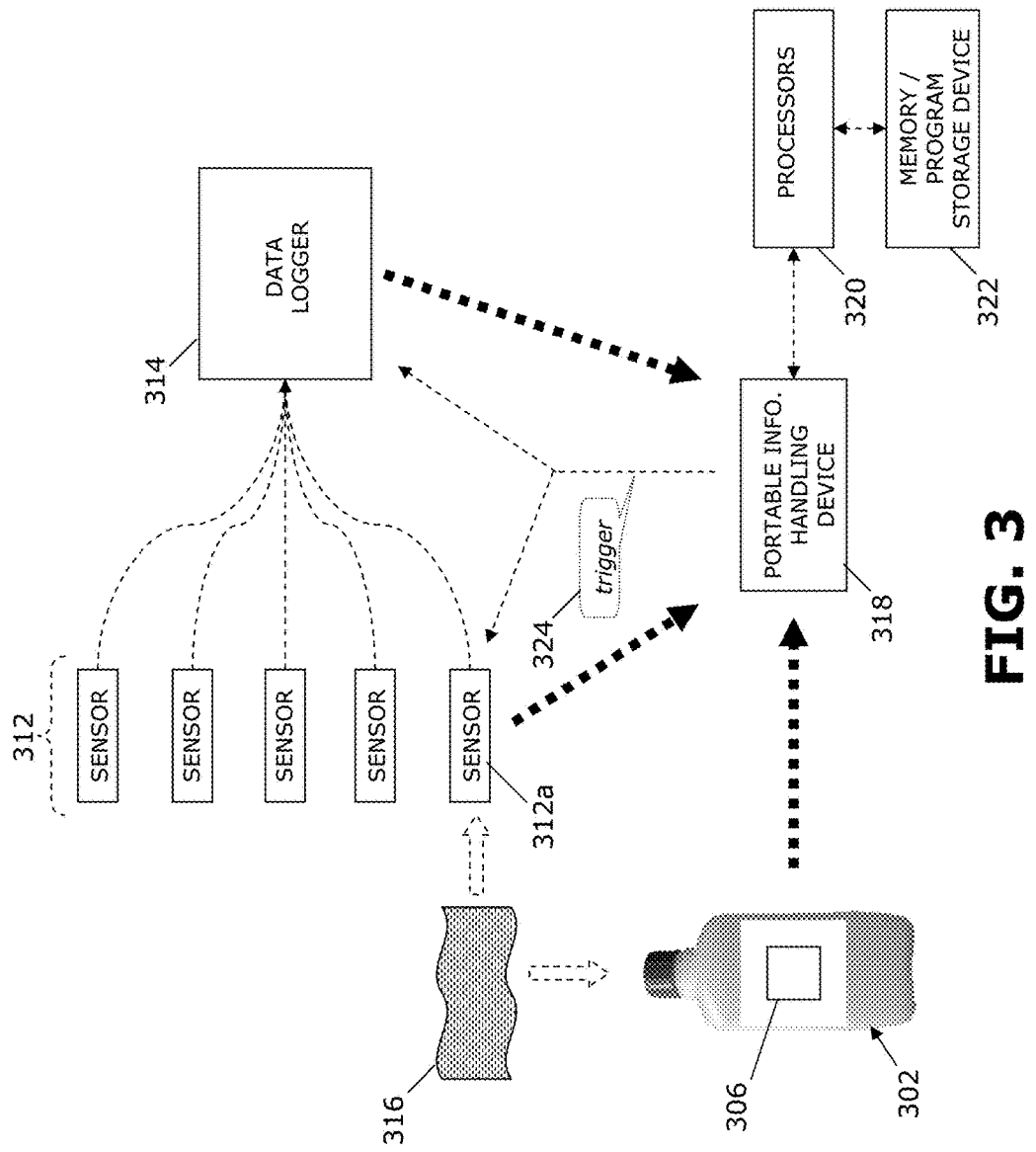
FIG. 3 schematically illustrates a working example of collecting data related to a water quality sample location.

FIG. 3 schematically illustrates a working example of collecting data related to a water quality sample location, in accordance with at least one embodiment of the invention.

As shown, a plurality of sensors 312 may be distributed at different measurement points (e.g., throughout a water supply network, such as in natural watercourses or in water propagation pipes). As noted hereabove, sensors 312 can be configured to measure turbidity, alkalinity and/or any of a variety of other water quality parameters. Measurements from the sensors 312 can be electronically transmitted to a data logger 314, via wired or wireless connections. Alternatively, a data logger 314 may not be present and data can be collected from each individual sensor 312.

In accordance with at least one embodiment of the invention, with respect to an individual sensor 312a disposed to measure a water quality parameter at a given portion of a watercourse (e.g., lake or river) 316, a container 302 may be used to accept a sample at substantially the same time that a measurement is taken by sensor 312a. A portable information handling device 318 may be used to identify the container 302 which contains the sample and to accept the measurement taken by sensor 312a.

In accordance with at least one embodiment of the invention, by way of illustrative and non-restrictive examples, the portable device 318 can be embodied, e.g., by a mobile phone (e.g., smartphone), tablet computer, laptop computer, digital camera with information storage capabilities, or a dedicated device for reading codes (as noted below) and which may include information storage capabilities. In at least one embodiment, the portable device 318 can include therein a utility or application (e.g., an installed mobile phone application) that performs any of the functions (associated with a portable device 318) as broadly described herein. An example portable device 318 that may be used in implementing embodiments herein includes one or more processors 320 and program code stored in memory or a non-signal program storage device 322. In this regard, a processor 320 may execute program instructions/code configured to perform functions of the portable device 318 described herein.

In accordance with at least one embodiment of the invention, by way of non-restrictive example, portable device 318 can be used to scan, or take a photograph of, a two-dimensional code 306 on container 302. The code 306 can indicate, among other things, a specific identifier (e.g., ID number) for the container 302 and an indication of the location where the sample was taken. (As such, the location may be pre-designated and may also be indicated via text on a label of container 302.) A timestamp can also be included when the device 318 is actuated to identify container 302. Additionally, portable device 318 can receive the aforementioned, substantially simultaneous measurement taken by sensor 312a, along with a timestamp and an identifier of the sensor 312a itself, via essentially any suitable connection (e.g., wireless). Alternatively, all such data can be received from a data logger 314 (if one is present). In either case, in accordance with a variant embodiment, the portable device 318 may be employed to actually trigger (324) the sensor 312a (either directly or via data logger 314) to take a measurement substantially simultaneously with accepting a water sample into container 302.

In accordance with at least one variant embodiment of the invention, sampling location data may be obtained from GPS (global positioning system) coordinates that may themselves be obtained from data logger 314 and/or sensor 312a. Further, the device 318 may itself be GPS-capable so that it can record location data and associate the same with container 302.

Figure 4:
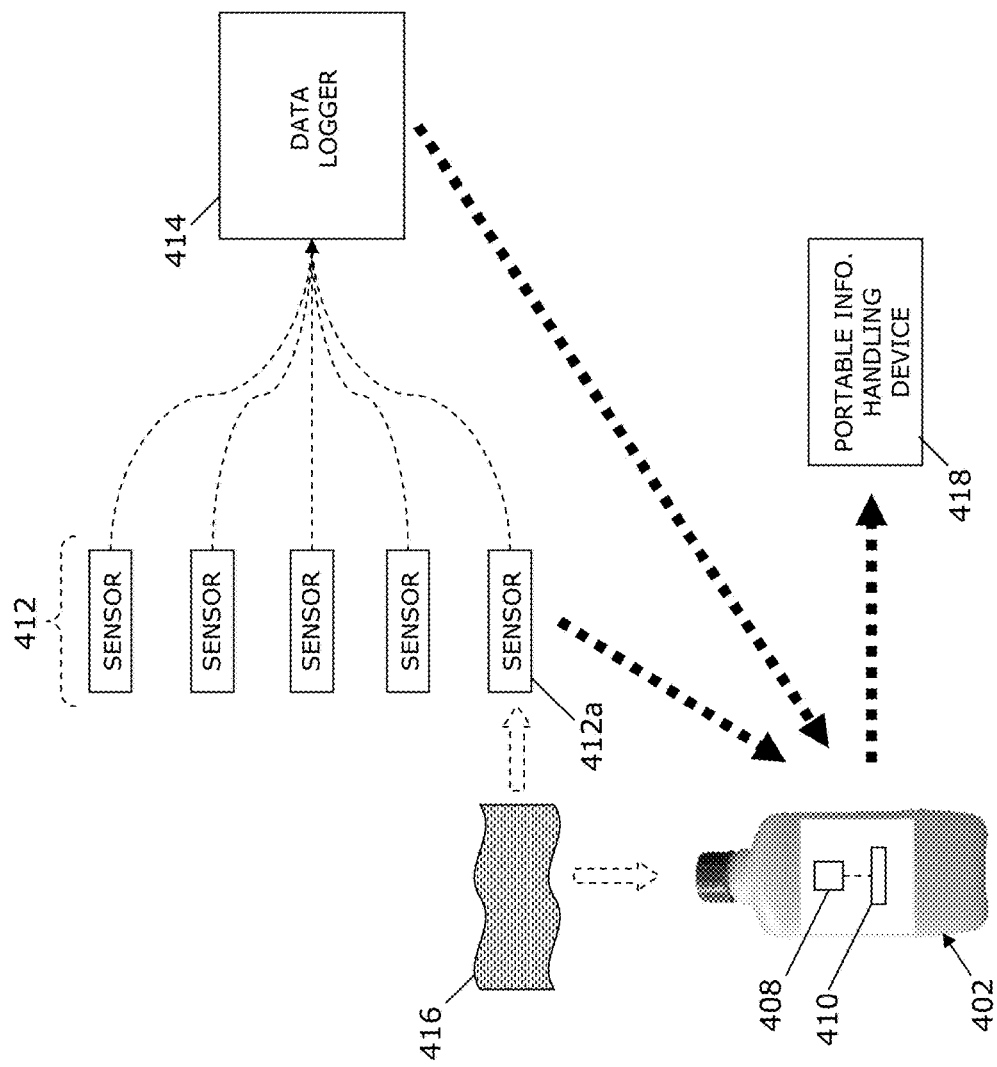
FIG. 4 schematically illustrates a working example of a variant embodiment of collecting data related to a water quality sample location.

FIG. 4 schematically illustrates, in accordance with at least one variant embodiment of the invention, a working example of collecting data related to a water quality sample location. Here, the arrangement is substantially the same as shown and described with respect to FIG. 3, except that sensor measurement data, taken by sensor 412a and transmitted directly therefrom or via a data logger 414, are stored via an RFID tag 408 of container 402 and its associated storage capability 410. In this manner, a portable information handling device 418 is not needed to receive such data, but still can be employed to identify the container 402 itself.

Figure 5:
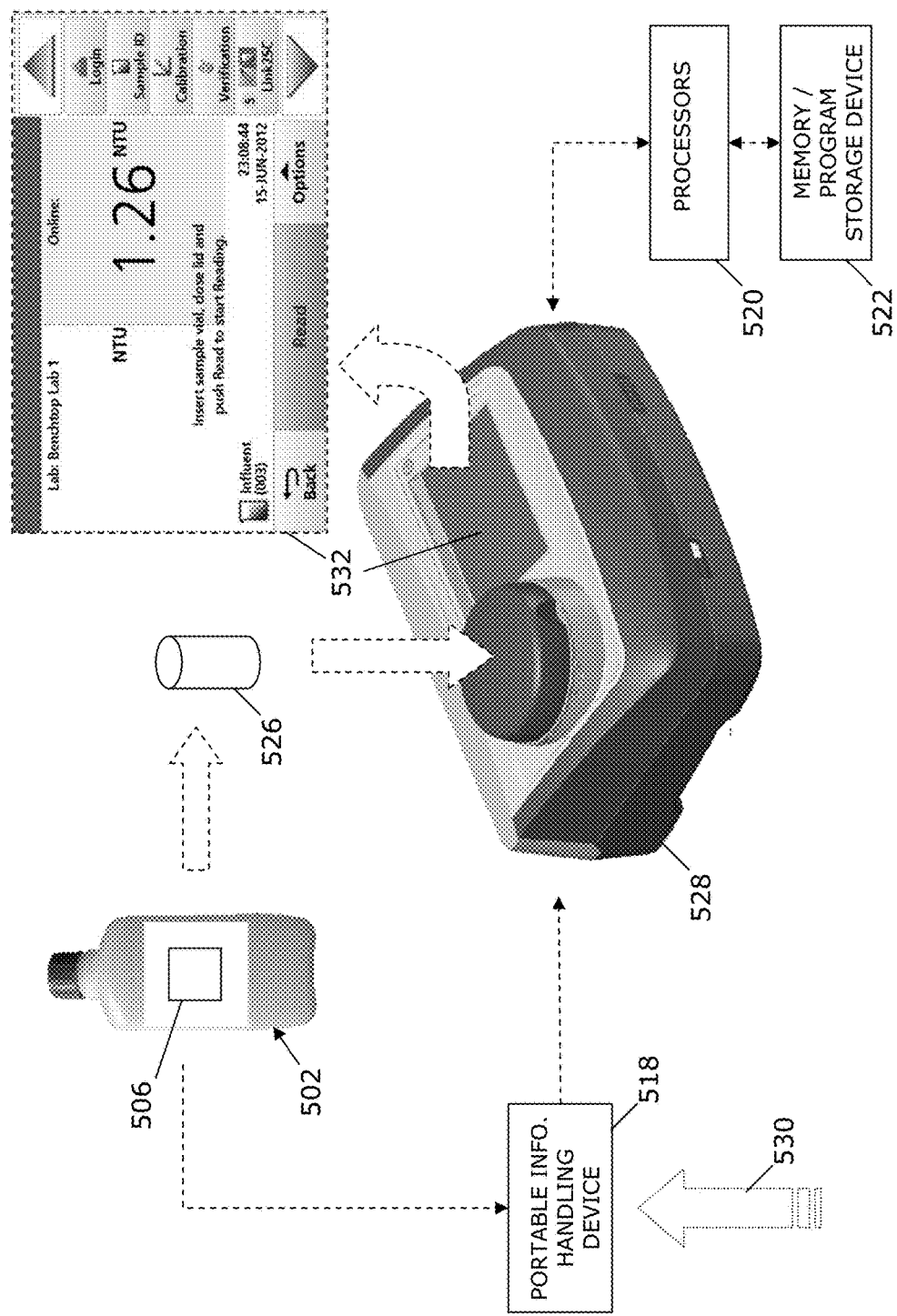
FIG. 5 schematically illustrates a working example of validating water quality sample data.

FIG. 5 schematically illustrates a working example of validating water quality sample data, in accordance with at least one embodiment of the invention. As touched on further above, a water quality sample collected in a container 502 can be tested via a measuring device, to verify the accuracy of a field sensor. Thus, as shown by way of merely illustrative example, at least a portion of a sample from container 502 can be placed in a vial 526 for testing in a laboratory tabletop measurement unit 528. By way of example, unit 528 could be configured to measure turbidity of the sample in vial 526.

In accordance with at least one embodiment of the invention, by way of illustrative and non-restrictive example, the laboratory measurement unit 528 may include information storage capabilities. As such, an example unit 528 that may be used in implementing embodiments herein includes one or more processors 520 and program code stored in memory or a non-signal program storage device 522. In this regard, a processor 520 may execute program instructions/code configured to perform functions of the unit 528 described herein.

In accordance with at least one embodiment of the invention, information relating to the sample container 502, and the sample contained therein, is transmitted to laboratory unit 528. This may be done by using a scanner or reader connected to or associated with the unit 528 itself, or can be downloaded to the unit 528 from a portable information handling device 518 that already includes information about the container 502 and its sample. In one embodiment, such information will have been obtained at an earlier time, e.g., via scanning a code 506 in a manner such as that described hereabove with respect to FIG. 3. In either eventuality, also transmitted to the unit 528 is information relating to a measurement taken by a field sensor, which can include a timestamp and an identifier of the sensor. Such information can come from the portable device 518, which itself can have been sent or uploaded thereto (530) in a manner similar to that described hereabove with respect to FIG. 3.

In accordance with at least one embodiment of the invention, laboratory unit 528 may include a display screen with user interface (532), embodied essentially in any suitable manner for showing values, side-by-side, from a transmitted sensor measurement and from a measurement (of vial 526) taken directly by unit 528. Based on this comparison, the associated field sensor can be validated and, if need be recalibrated. In accordance with one embodiment, the portable device 518 can carry at least one item of recalibration information back to a field sensor or data logger, and transmit thereto the recalibration information that can assist in resetting the field sensor.

FIG. 6 schematically illustrates, in accordance with at least one variant embodiment of the invention, a working example of validating water quality sample data. Here, the arrangement is substantially the same as shown and described with respect to FIG. 5, except that sensor measurement data, taken by a field sensor and transmitted directly therefrom or via a data logger, will have been stored via an RFID tag 608 of container 602 and its associated storage capability 610. (See, e.g., the example of FIG. 4 herein.) In this manner, a portable information handling device is not needed to transmit such data to a lab unit 628. Information relating to the sample container 602, and the sample contained therein, can be transmitted to laboratory unit 628 via a scanner or reader connected to or associated with the unit 628. In a variant embodiment, sensor measurement data can be transmitted to lab unit 628 via another medium, such as wireless or wired communication.

In accordance with at least one variant embodiment of the invention, with respect to any and all of the contexts set forth heretofore with respect to FIGS. 1-6 or to any other operating context, it is conceivable to run a consistency check of any collected data with respect to the same sample container. For instance, a type of flag or warning (e.g., a pop-up window in a portable device) can be triggered if, with respect to one and the same sample container, a field sensor measurement is taken: at a different GPS (global positioning system) position than a previous time; and/or from a sensor with a different sensor ID than a previous time. A warning could also be triggered if one or more sensor measurement values significantly differ from a historical trend or with respect to a historical window (e.g., the last five measurements taken by the sensor).

It can be appreciated from the foregoing that, in accordance with at least one embodiment of the invention, a kit can be realized which includes different components. Such a kit can include a container for obtaining a water sample from a location measured by a water quality sensor with the container including electronically readable identifying information. The kit can also include an apparatus which, by way of an illustrative and non-restrictive example, can be a laboratory measurement unit as broadly described and contemplated herein. Such an apparatus, however embodied, can receive measurement data from the water quality sensor and identifying information for the container, match the measurement data from the water quality sensor with the identifying information for the container, obtain additional measurement data from testing of the water sample from the container, and validate the water quality sensor via comparing the measurement data from the water quality sensor with the additional measurement data. In one embodiment, the kit can further include a mobile device application which reads the electronically readable identifying information of the container.

FIG. 7 sets forth a process more generally for collecting data related to a water quality sample location, in accordance with at least one embodiment of the invention. As shown in FIG. 7, identifying information of a water quality sample container is electronically obtained (701), and identifying information of a water quality sample location is electronically obtained (703). There is placed, in the container, a water sample from the water quality sample location (705). There is stored the identifying information of the water quality sample container and the identifying information of the water quality sample location (707); such storing includes associating the identifying information of the water quality sample container and the identifying information of the water quality sample location (709).

FIG. 8 sets forth a process more generally for validating water quality sample data, in accordance with at least one embodiment of the invention. As shown in FIG. 8, measurement data obtained by a water quality sensor are received (811). There is obtained identifying information for a container which contains a water sample from a location measured by the water quality sensor (813). The water quality sensor is validated via: matching the measurement data obtained by the water quality sensor with the identifying information for the container (815); testing the water sample from the container, and thereby obtaining additional measurement data (817); and comparing the measurement data obtained by the water quality sensor with the additional measurement data from the testing (819).

In accordance with at least one embodiment of the invention, any of a great variety of sensors may be employed in the contexts and settings broadly described and contemplated herein, let alone in any of a variety of analogous contexts and settings. The ensuing discussion thus includes a focus on sensors in particular, which may be employed, inter alia, as the sensors indicated at 312 in FIG. 3 and at 412 in FIG. 4. Also included herebelow is some discussion on processing data derived from sensors.

In accordance with at least one embodiment of the invention, sensors can be configured and disposed to measure ammonium, nitrate, dissolved oxygen, turbidity, temperature, and/or suspended solids in a manner, inter alia, to carry out measurements as described generally herein. Through any of a variety of mechanisms, they may be in ready communication with a data logger (e.g., as described and illustrated with respect to FIG. 3 or 4) or more generally with essentially any digital processing unit (i.e., gateway), which itself may be in communication with a central database system (e.g., that could be internet hosted or locally hosted).

In accordance with at least one embodiment of the invention, sensors as employed herein may be configured to self-diagnose their own health through any suitable arrangement. By way of illustrative example, such self-diagnosis could be performed via an internal probing operation of the sensor, whereby sensor inputs and outputs are continually monitored, and whereby one or more tailored algorithms are applied. Such algorithms, when applied, could calculate wear and tear on parts as well as detect or discern any outputs that would be considered out of a prescribed "normal" range of acceptable parameters. Thus, referring to the examples set forth heretofore, sensors 312 (in FIG. 3) or 412 (in FIG. 4) may operate to perform such self-diagnosis.

In accordance with at least one embodiment of the invention, if, on the basis of self-diagnosis, something is determined to breach a predetermined threshold related to acceptable operating parameters, an arrangement in the sensor (e.g., an operable algorithm that may be built in to or associated with internal logic) may forecast the length of time that sensor readings can be safely relied upon. This forecast may then be communicated to another location (e.g., a data logger 312 or 412 as described and illustrated with respect to FIGS. 3 and 4), wherefrom an end user may generally monitor the health of sensors simultaneously with accepting field measurements from the sensors. Alternatively, raw data from each sensor can be processed at another location where a prediction, as just described, may be made. In either scenario, an alert may be generated respective to any predetermined conditions (e.g., x days remaining until a sensor is forecast to stop functioning), to prompt an end user to take further action. By way of merely illustrative example, such conditions may include, but need not be limited to, unforeseen breakage or disablement of one or more internal components, e.g., as maybe monitored by considering any of a variety of parameters such as voltage, or other digital or electronic "flags".

In accordance with at least one embodiment of the invention, a processing location (e.g., a data logger as described herein, or a central database system), in addition to tracking sensor self-diagnosis as just described, may act to track and monitor the length of time since any predetermined maintenance procedures may have last been performed with respect to the sensors. To this end, the processing location may be pre-loaded with any data that would help establish parameters for such maintenance procedures, e.g., a prescribed time interval for checking or otherwise performing a maintenance task with respect to each sensor. The processing location may employ these parameters in any desired manner, e.g., to generate an alert in advance for when an upcoming maintenance procedure may be due. Merely by way of illustrative example, such procedures may include replacement of parts (or subparts) of probes associated with the sensor that may well undergo wear and tear over time, or general calibrations that may be performed in accordance with a predetermined schedule (that itself is not necessarily related to internal self-diagnosis).

In accordance with at least one embodiment of the invention, once a processing location (e.g., a data logger or central database system) generates or processes an alert (e.g., driven by sensor self-diagnosis or by maintenance considerations as described above), an end user (or group thereof) may receive these alerts immediately. In this connection, such alerts may be delivered by essentially any suitable mechanism, such as via email or via a mobile device user interface. (In the latter scenario, an application may be installed on the mobile device, specifically for receiving and processing such alerts). Reference may be made to the discussion heretofore of portable information handling devices (e.g., as indicated at 318 and 418 in FIGS. 3 and 4, respectively) as another example of a medium through which an end user may receive alerts; otherwise, the end user may still receive alerts through a stationary (e.g., desktop) computer, assuming the same has a connection (wired or wireless) to the aforementioned processing location. Any associated notification messages may be structured to describe or indicate the severity of any alert.

To this end, in accordance with at least one embodiment of the invention, alerts may take any of a great variety of forms, e.g., based on different levels of severity. For instance, a "critical" severity signal can indicate that a sensor is in a state requiring immediate intervention or action in order to return to a normal operating state. If such intervention or action is not undertaken within a predetermined time frame, then a "severe" state condition can be communicated via an alert. By way of illustrative example, a "critical" alert can relate to a condition where viable sensor measurements are still possible, while a "severe" alert can relate to a condition where sensor measurements cannot be regarded as accurate or reliable (especially to the extent that restorative action may not have been undertaken). In either case, "critical" or "severe", the corresponding notification message can include a dedicated color or other signal, e.g., a yellow or red color, respectively, may be conveyed via a user interface or a flashing light. Generally, any notification messages associated with alerts may also indicate to the end user one or more suggested actions that would help return a sensor to a state of normal operation.

In that vein, in accordance with at least one embodiment of the invention, merely by way of illustrative example, the notification message may suggest a routine maintenance procedure such as generally cleaning the sensor, wiping off any buildup on a measuring electrode, or replacement of a cap or cartridge. Other suggested actions could include, e.g., a need to undertake a calibration procedure such as mobile sensor verification against a laboratory instrument (e.g., as described itself in particular hereabove with relation to FIGS. 3-6), "air calibration" in order to adjust a measuring slope (e.g., as a "zeroing" calibration for a sensor via taking a reading from the air), or "point calibration" based on a laboratory procedure. (In point calibration, merely by way of illustrative example, a sample may be collected, brought into a laboratory, and analyzed using laboratory equipment; results between sensor measurements and laboratory measurements may be compared, and a sensor may then be adjusted or recalibrated based on the laboratory reading.)

In accordance with at least one embodiment of the invention, if an end user chooses to pursue a suggested action, he/she may indicate as much via a prompt back to the processing location. At this point, the processing location may send instructions to the user via the same medium as the prior notification(s); especially in the case of a mobile device (or portable information handling device, as indicated at 318 and 418 in FIGS. 3 and 4), the end user may then be able to perform the suggested action in the field, right at the location of the affected sensor (e.g., cleaning a portion of the sensor or replacing a damaged or missing part). Such action may include sensor calibration of the type described heretofore with reference to FIGS. 3 and 4, e.g., the user may then trigger (324) a sensor to take a measurement substantially simultaneously with accepting a water sample into a container. The end user can otherwise be prompted to undertake other calibration actions, such as those that may generally involve field sample collection, delivery of the sample to a laboratory, and testing in the laboratory. Here, a technician in the laboratory may also be able tin input results of sample analysis (in the laboratory) into the processing location via an interface as described heretofore (e.g., a portable information handling device, such as that indicated at 518 and 618 in FIGS. 5 and 6).

In accordance with at least one embodiment of the invention, in connection with the capabilities discussed hereabove, an end user may be provided with one or more options to permit the continuous provision of sensor measurements to a third party control system (e.g., SCADA [supervisory control and data acquisition] or HMI [human-machine interface]) in a normal (stable) range, while calibrations continue to be performed; by way of example, a processing location as discussed heretofore may serve as a "relay" to send measurements to such control systems. Such options can be provided via a user interface on a mobile device, other portable information handling device, or other interface (e.g., via a desktop computer). The processing center can store any related options chosen by the end user such that once calibrations are made, any necessary connections with third party control systems can be made or reestablished such as to undertake (or resume) their receipt of sensor measurement data after a defined period of time.

In accordance with at least one embodiment, it should be appreciated and understood that a group of end users may collaborate on ensuring the continued accuracy and functionability of measurement sensors. The processing location may keep records of all interactions and interventions of different users with sensors. Thus, such information may be shared among the group to avoid duplicative effort, while the processing location may apply any desired level of access management to ensure that only authorized end users are able to participate in the management, calibration and maintenance of sensors in accordance with any predetermined protocol.

Figure 9:
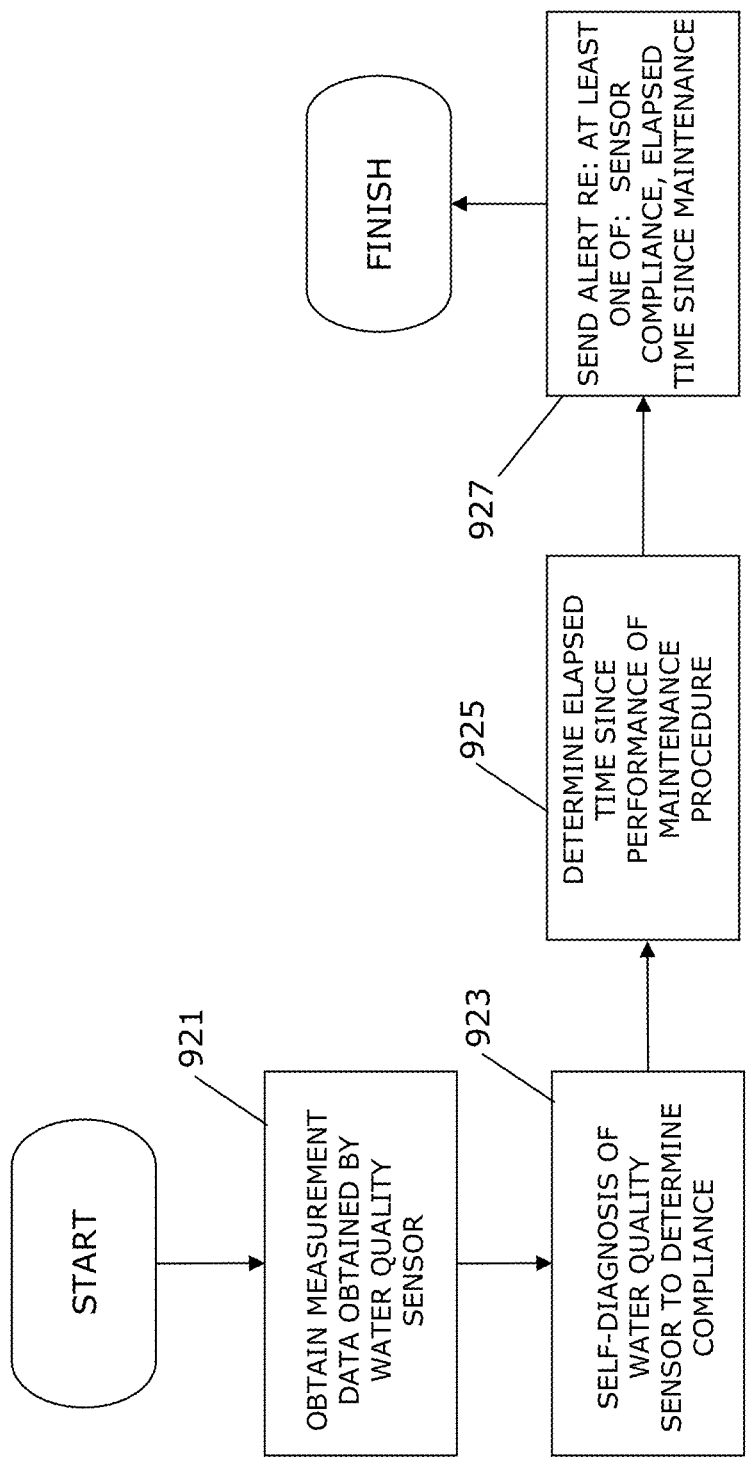
FIG. 9 sets forth a process more generally for managing data from a water quality sensor.

FIG. 9 sets forth a process more generally for managing data from a water quality sensor, in accordance with at least one embodiment of the invention. As shown in FIG. 9, measurement data obtained by a water quality sensor are obtained (921). Self-diagnosis of the water quality sensor may be performed via determining compliance with one or more predetermined operating parameters (923). There may be determined an elapsed time since performance of a maintenance procedure relative to the water quality sensor (925). An alert is sent to an end user relative to at least one of: compliance of the water quality sensor with one or more predetermined operating parameters, and an elapsed time since performance of a maintenance procedure relative to the water quality sensor (927).

It can be appreciated from the foregoing that electronic components of one or more systems or instruments may include, but are not limited to, at least one processing unit, a memory, and a communication bus or communication means that couples various components including the memory to the processing unit(s). A system or instrument may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data.

In the examples described and contemplated herein, a user may interface with (for example, enter commands and information) an instrument through input devices. A display device can also be included with an instrument. In addition to a display device, the instrument may also include other input and/or output devices, e.g., analog and/or digital/logical. The instrument may operate in a networked or distributed environment using logical connections to other devices or databases. The devices may use logical connections with the instrument, and the logical connections may include a network, such local area network (LAN) or a wide area network (WAN), or wireless networks, but may also include other networks/buses.

As will be appreciated by one skilled in the art, aspects may be embodied as a system, method or program product. Accordingly, aspects may take the form of an entirely hardware embodiment, or an embodiment including software (including firmware, resident software, micro-code, etc.) that may all generally be referred to herein as a "circuit," "module" or "system." Furthermore, embodiments may take the form of a program product embodied in at least one device readable medium having device readable program code embodied thereon.

Any combination of device readable storage medium(s) may be utilized. In the context of this document, a device readable storage medium ("storage medium") may be any tangible, non-signal medium that can contain or store a program comprised of program code configured for use by or in connection with an instruction execution system, apparatus, or device.

The detailed descriptions of the above example embodiments are not exhaustive descriptions of all embodiments contemplated. Indeed, persons with ordinary skill in the art will recognize that certain elements of the above-described example embodiments may variously be combined or omitted to create further embodiments, and such further embodiments fall within the scope and teachings of the invention. It will also be apparent to those of ordinary skill in the art that the above-described embodiments may be combined in whole or in part to create additional embodiments. Various example embodiments are disclosed in the APPENDIX.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments have been described herein, including the non-limiting examples provided in the figures, it is to be understood that the embodiments are not limited to those precise example embodiments, and that various other changes and modifications may be affected therein by one skilled in the art without departing from the scope or spirit of the disclosure.

APPENDIX

An embodiment provides an apparatus comprising: one or more processors; a program storage device tangibly embodying a program of instructions that when executed by the one or more processors enables the apparatus to: receive information related to the identification of a water quality sample container; receive information related to the identification of a predetermined water quality sample location; store the information related to the identification of the water quality sample container and the information related to the identification of the predetermined water quality sample location.

In an embodiment, the program storage device further enables the apparatus to receive measurement data obtained by a water quality sensor which measures water quality at the predetermined water quality sample location.

In an embodiment, to store comprises associating the measurement data from the water quality sensor with the information related to identification of the water quality sample container and the information related to identification of the water quality sample location.

In an embodiment, to receive measurement data comprises triggering the water quality sensor to receive a measurement.

In an embodiment, to receive measurement data comprises obtaining the measurement data from a source other than the water quality sensor.

In an embodiment, the source other than the water quality sensor comprises a data logger in communication with the water quality sensor.

In an embodiment, to receive measurement data comprises receiving the measurement data at a mobile device.

In an embodiment, to receive measurement data comprises writing the measurement data to a storage medium physically associated with the container.

In an embodiment, wherein the storage medium physically associated with the container comprises an RFID tag.

In an embodiment, to receive information related to the identification of a water quality sample container comprises electronically reading an identifier of the container.

In an embodiment, to read comprises reading at least one of: a two-dimensional code and an RFID tag.

In an embodiment, to read comprises reading via a mobile device.

An embodiment provides an apparatus comprising: one or more processors; a program storage device tangibly embodying a program of instructions that when executed by the one or more processors enables the apparatus to: receive information related to water quality contained with a water quality sample container; receive information related to identification of a predetermined water quality sample location; receive information related to water quality of a sample obtained from the predetermined water quality sample location; compare the information related to water quality contained with a water quality sample container and the information related to water quality of a sample obtained from the predetermined water quality sample location; and provide an indication of a result of the comparison.

In an embodiment, to receive information related to water quality contained with a water quality sample container comprises electronically reading an identifier of the container.

In an embodiment, to receive information related to water quality of a sample obtained from the predetermined water quality sample location comprises downloading the measurement data from at least one of: a mobile device and a storage medium physically associated with the container.

An embodiment provides a method comprising: electronically obtaining identifying information of a water quality sample container; electronically obtaining identifying information of a water quality sample location; placing, in the container, a water sample from the water quality sample location; and storing the identifying information of the water quality sample container and the identifying information of the water quality sample location; the storing comprising associating the identifying information of the water quality sample container and the identifying information of the water quality sample location.

In an embodiment, there is further included obtaining measurement data obtained by a water quality sensor which measures water quality at the water quality sample location.

In an embodiment, the storing comprises associating the measurement data from the water quality sensor with the identifying information of the water quality sample container and the identifying information of the water quality sample location.

In an embodiment, the obtaining of measurement data comprises triggering the water quality sensor to take a measurement.

In an embodiment, the obtaining of measurement data comprises obtaining the measurement data from a source other than the water quality sensor.

In an embodiment, the source other than the water quality sensor comprises a data logger in communication with the water quality sensor.

In an embodiment, the obtaining of measurement data comprises receiving the measurement data at a mobile device.

In an embodiment, the obtaining of measurement data comprises writing the measurement data to a storage medium physically associated with the container.

In an embodiment, the storage medium physically associated with the container comprises an RFID tag.

In an embodiment, the water quality sensor is configured to perform self-diagnosis.

In an embodiment, the water quality sensor is configured to perform self-diagnosis via determining compliance with one or more predetermined operating parameters.

In an embodiment, there is included determining a remaining useful life of the water quality sensor based on the self-diagnosis.

In an embodiment, there is included determining an elapsed time since performance of a maintenance procedure relative to the water quality sensor.

In an embodiment, there is included sending an alert to an end user relative to at least one of: compliance of the water quality sensor with one or more predetermined operating parameters; and an elapsed time since performance of a maintenance procedure relative to the water quality sensor.

In an embodiment, the sending comprises sending an alert to a portable information handling device.

In an embodiment, the sending comprises sending a notification message conveying information relative to the alert.

In an embodiment, the sending of a notification message comprises conveying a degree of severity of the alert.

In an embodiment, the sending of a notification message comprises conveying suggested compensatory action relative to the alert.

In an embodiment, the suggested compensatory action includes a suggested maintenance procedure.

In an embodiment, the suggested compensatory action includes a suggestion for calibration of the water quality sensor.

In an embodiment, there is included sending instructions relative to the compensatory action upon receipt of a notification from the end user.

In an embodiment, there is included sending a notification to the end user which presents an option for continuing transmission of measurement data from the water quality sensor to a third party control system.

In an embodiment, the obtaining of identifying information of the container comprises electronically reading an identifier of the container.

In an embodiment, the reading comprises reading at least one of: a two-dimensional code and an RFID tag.

In an embodiment, the reading is performed via a mobile device.

In an embodiment, the steps of obtaining identifying information and placing a water sample in the container are performed substantially simultaneously.

In an embodiment, the identifying information of the water quality sample location includes global positioning system coordinates and a timestamp.

In an embodiment, the identifying information of the water quality sample container includes a unique ID number.

An embodiment provides a method comprising: receiving measurement data obtained by a water quality sensor; obtaining identifying information for a container which contains a water sample from a location measured by the water quality sensor; validating the water quality sensor via: matching the measurement data obtained by the water quality sensor with the identifying information for the container; testing the water sample from the container, and thereby obtaining additional measurement data; and comparing the measurement data obtained by the water quality sensor with the additional measurement data from the testing.

In an embodiment, the obtaining of identifying information comprises electronically reading an identifier of the container.

In an embodiment, the receiving of measurement data comprises receiving identifying information of the location measured by the water quality sensor.

In an embodiment, the receiving of the measurement data comprises downloading the measurement data from at least one of: a mobile device and a storage medium physically associated with the container.

In an embodiment, there is further included sending corrected calibration data to the water quality sensor upon comparing the measurement data obtained by the water quality sensor with the additional measurement data from the testing.

An embodiment provides a program storage device storing program code executable by one or more processors, the program code comprising: program code configured to electronically obtain identifying information of a water quality sample container; program code configured to electronically obtain identifying information of a water quality sample location at which a water sample is placed in the container; and program code configured to store the identifying information of the water quality sample container and the identifying information of the water quality sample location, via associating the identifying information of the water quality sample container and the identifying information of the water quality sample location.

In an embodiment, there is further included program code configured to obtain measurement data obtained by a water quality sensor which measures water quality at the water quality sample location.

In an embodiment, there is further included program code configured to trigger the water quality sensor to take a measurement.

In an embodiment, the program code is configured to obtain the identifying information of the container via electronically reading an identifier of the container.

An embodiment provides a program storage device storing program code executable by one or more processors, the program code comprising: program code configured to receive measurement data obtained by a water quality sensor; program code configured to obtain identifying information for a container which contains a water sample from a location measured by the water quality sensor; program code configured to validate the water quality sensor via: matching the measurement data obtained by the water quality sensor with the identifying information for the container; testing the water sample from the container, and thereby obtaining additional measurement data; and comparing the measurement data obtained by the water quality sensor with the additional measurement data from the testing.

In an embodiment, to receive the measurement data comprises receiving identifying information of the location measured by the water quality sensor.

In an embodiment, to receive the measurement data comprises downloading the measurement data from at least one of: a mobile device and a storage medium physically associated with the container.

An embodiment provides a kit comprising: a container for obtaining a water sample from a location measured by a water quality sensor, the container comprising electronically readable identifying information; and an apparatus which: receives measurement data from the water quality sensor and identifying information for the container; matches the measurement data from the water quality sensor with the identifying information for the container; obtains additional measurement data from testing of the water sample from the container; and validates the water quality sensor via comparing the measurement data from the water quality sensor with the additional measurement data.

In an embodiment, the container comprises an identifier which provides the electronically readable identifying information.

In an embodiment, there is further included: a mobile device application which obtains measurement data from the water quality sensor; wherein the receiving of measurement data comprises receiving measurement data obtained by the mobile device application.

In an embodiment, there is further included: a mobile device application which reads the electronically readable identifying information of the container; wherein the receiving of identifying information from the container comprises receiving identifying information read by the mobile device application.

In an embodiment, the apparatus further sends corrected calibration data to the water quality sensor upon comparing the measurement data from the water quality sensor with the additional measurement data.

An embodiment provides an apparatus comprising: a water quality sample container; a electronic storage medium physically associated with the water quality sample container; and an identifier which provides electronically readable identifying information of the water quality sample container; the electronic storage medium being configured to store information related to a water quality sample from a predetermined location.

In an embodiment, the identifier and the storage medium comprise a shared component.

In an embodiment, the shared component comprises an RFID tag.

In an embodiment, the electronic storage medium comprises an RFID tag.

In an embodiment, the identifier comprises a two-dimensional code.

In an embodiment, the identifier comprises an RFID tag.

In an embodiment, the storage medium is configured to store information related to a water quality sample measured by a sensor at the predetermined location.

In an embodiment, the storage medium is configured to store information related to the sensor which measures the water quality sample at the predetermined location.

In an embodiment, the storage medium is configured to store information related to at time at which the sensor which measures the water quality sample at the predetermined location.

In an embodiment, the storage medium is configured to store information related to a time at which the container is removed from a vicinity of the sensor.

What is claimed is:
1. An apparatus comprising:
one or more processors;
a program storage device tangibly embodying a program of instructions that when executed by the one or more processors enables the apparatus to:
receive information related to the identification of a water quality sample container comprising a water sample from a water source;
receive information related to the identification of a predetermined water quality sample location associated with the water quality sample;
receive, via an electronic transmission from one or more sensors located proximate to the predetermined water quality sample location and within the water source, a measurement taken from the water source, by the one or more sensors, and related to a parameter of the water source, wherein the measurement is taken at substantially the same time as the water sample is accepted by the water quality sample container;
store the information related to the identification of the water quality sample container, the information related to the identification of the predetermined water quality sample location, the measurement, and an identifier of the one or more sensors providing the measurement;
determine a calibration status of the one or more sensors within the water source by validating the measurement received from the one or more sensors with the corresponding measurement taken from the water quality sample by comparing the measurement received from the one or more sensors with a corresponding measurement taken from the water quality sample; and recalibrate the one or more sensors responsive to determining the calibration status of the one or more sensors is uncalibrated, wherein the automatically recalibrating comprises electronically transmitting recalibration information, obtained based upon the validating, to the one or more sensor identified using the identifier.

2. A method comprising:
electronically obtaining identifying information of a water quality sample container;
electronically obtaining identifying information of a water quality sample location;
placing, in the container, a water sample from a water source at the water quality sample location;
receiving, via an electronic transmission from one or more sensors located proximate to the predetermined water quality sample location and within the water source, a measurement taken from the water source, by the one or more sensors, and related to a parameter of the water source, wherein the measurement is taken at substantially the same time as the water sample is accepted by the water quality sample container;
storing the identifying information of the water quality sample container, the identifying information of the water quality sample location, the measurement, and an identifier of the one or more sensors providing the measurement;
said storing comprising associating the identifying information of the water quality sample container, the identifying information of the water quality sample location, the measurement, and the identifier;
determine a calibration status of the one or more sensors within the water source by validating the measurement received from the one or more sensors with the corresponding measurement taken from the water quality sample by comparing the measurement received from the one or more sensors with a corresponding measurement taken from the water quality sample; and
recalibrating the one or more sensors responsive to determining the calibration status of the one or more sensors is uncalibrated, wherein the automatically recalibrating comprises electronically transmitting recalibration information, obtained based upon the validating, to the one or more sensors identified using the identifier.

3. The method according to claim 2, wherein the one or more sensors comprise one or more water quality sensors which measure water quality at the water quality sample location.

4. The method according to claim 3, wherein the water quality sensor is configured to perform self-diagnosis.

5. The method according to claim 3, comprising determining an elapsed time since performance of a maintenance procedure relative to the water quality sensor.

6. The method according to claim 3, comprising sending an alert to an end user relative to at least one of: compliance of the water quality sensor with one or more predetermined operating parameters; and an elapsed time since performance of a maintenance procedure relative to the water quality sensor.

7. The method according to claim 2, wherein the receiving comprises triggering the water quality sensor to take a measurement.

8. The method according to claim 2, wherein the receiving comprises receiving the measurement from a source other than the water quality sensor.

9. The method according to claim 8, wherein the source other than the water quality sensor comprises a data logger in communication with the water quality sensor.

10. The method according to claim 2, wherein the receiving comprises receiving the measurement at a mobile device.

11. The method according to claim 2, wherein the receiving comprises writing the measurement data to a storage medium physically associated with the container.

12. The method according to claim 11, wherein the storage medium physically associated with the container comprises an RFID tag.

13. The method according to claim 2, wherein said obtaining of identifying information of the container comprises electronically reading an identifier of the container.

14. The method according to claim 13, wherein said reading comprises reading at least one of: a two-dimensional code and an RFID tag.

15. The method according to claim 14, wherein said reading is performed via a mobile device.

16. The method according to claim 2, wherein said steps of obtaining identifying information and placing a water sample in the container are performed substantially simultaneously.

17. The method according to claim 2, wherein the identifying information of the water quality sample location includes global positioning system coordinates and a timestamp.

18. The method according to claim 2, wherein the identifying information of the water quality sample container includes a unique ID number.

19. A program product, comprising:
a storage device having program code stored therewith, the program code being executable by one or more processors, said program code comprising:
program code configured to electronically obtain identifying information of a water quality sample container comprising a water sample from a water source;
program code configured to electronically obtain identifying information of a water quality sample location at which a water sample is placed in the container;
program code configured to receive, via an electronic transmission from one or more sensors located proximate to the predetermined water quality sample location and within the water source, a measurement taken from the water source, by the one or more sensors, and related to a parameter of the water source, wherein the measurement is taken at substantially the same time as the water sample is accepted by the water quality sample container;
program code configured to store the identifying information of the water quality sample container, the identifying information of the water quality sample location the measurement, and an identifier of the one or more sensors providing the measurement, via associating the identifying information of the water quality sample container, the identifying information of the water quality sample location, the measurement, and an identifier of the one or more sensors providing the measurement; and
program code configured to determine a calibration status of the one or more sensors within the water source by validating the measurement received from the one or more sensors with the corresponding measurement taken from the water quality sample by comparing the measurement received from the one or more sensors with a corresponding measurement taken from the water quality sample; and
program code configured to recalibrate the one or more sensors responsive to determining the calibration status of the one or more sensors is uncalibrated, wherein the automatically recalibrating comprises electronically transmitting recalibration information, obtained based upon the validating, to one or more sensors identified using the identifier.

\* \* \* \* \*